(12) United States Patent
Uckun et al.

(10) Patent No.: US 6,605,589 B1
(45) Date of Patent: Aug. 12, 2003

(54) CATHEPSIN INHIBITORS IN CANCER TREATMENT

(75) Inventors: Fatih M. Uckun, White Bear Lake, MN (US); De-Min Zhu, Mounds View, MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

(21) Appl. No.: 09/539,739

(22) Filed: Mar. 31, 2000

(51) Int. Cl.$^7$ ............... A01N 37/18; A01N 38/00; A01N 33/18; A01N 33/24; A61K 38/28; A61K 31/04

(52) U.S. Cl. ............... 514/2; 514/4; 514/740

(58) Field of Search ............... 514/475, 2, 4, 514/740

(56) References Cited

U.S. PATENT DOCUMENTS 5,883,121 A    3/1999  Yamashita et al.

FOREIGN PATENT DOCUMENTS

| WO | WO 98/49190 | 11/1998 |
|---|---|---|
| WO | WO 01/44464 | 6/2001 |

OTHER PUBLICATIONS

Leto, G. et al., "Effects of E–64 (Cysteine–Proteinase Inhibitor) and Pepstatin (Aspartyl–Proteinase Inhibitor) on Metastasis Formation in Mice with Mammary and Ovarian Tumors", In Vivo, vol. 8, pp. 231–236, 1994.*

Xing, R. et al., "Control of Breast Tumor Cell Growth Using a Targeted Cysteine Protease Inhibitor", Cancer Res., vol. 58, pp. 904–909 (1998).*

Sivaparvathi et al., "Expression of cathepsin D during the progression of human gliomas", Neurosci. Lett., vol. 208, pp. 179–174, 1996.*

Soderstrom, K–O. et al., "Expression of Acid cysteine Proteinase Inhibitor (ACPI) in the Normal Human Prostate, Benign Prostatic Hyperplasia and Adenocarcinoma", Int. J. Cancer, vol. 62, pp. 1–4 (1995).*

Krueger, S., Haeckel, C., Buehling, F., and Roessner, A. (1999) "Inhibitory Effects of Antisense Cathepsin B cDNA Transfection on Invasion and Motility in a Human Osteosarcoma Cell Line". Cancer Research, 59:6010–6014.

Zhu, D.–M. and Uckun, F.M. (2000) "Z–Phe–Gly–NHO–Bz, an Inhibitor of Cysteine Cathepsins, Induces Apoptosis in Human Cancer Cells", Clinical Cancer Research, 6:2064–2069.

Zhu, D.–M. and Uckun, F.M. (2000) "Cathepsin Inhibition Induces Apoptotic Death in Human Leukemia and Lymphoma Cells". Leukemia and Lymphoma, 39:343–354.

Blandino GB, Levine AJ, Oren M (1999). Mutuant p53 gain of function: differential effects of different p53 mutants on resistance of cultured cells to chemotherapy. Onogene 18: 477–485.

Brimmell M, Mendiola R, Mangion J, Packham G (1998). BAX frameshift mutations in cell lines derived from human haemopoietic malignancies are associated with resistance to apoptosis and microsatellite instability. Oncogene 16: 1803–1812.

Chow SC, Weiss M, Kass GE, Holmstrom TH, Eriksson JE, Orrenius S (1995). Involvement of multiple proteases during Fas–mediated apoptosis in T lymphocytes. FEBS Lett 364: 134–138.

Cordone I, Masi S, Mauro FR, Soddu S, Morsilli O, Valentini T, Vegna ML, Guglielmi C, Mancini F, Guiliacci S, Sacchi A, Mandelli F, Foa R (1998). p53 Expressions in B–cell chronic lymphocytic leukemia: a marker of disease progression and poor prognosis. Blood 91: 4342–4349.

Demuth, HU, Schierhorn A, Bryan P, Hofke R, Kirschke H, and Bromme D (1996). N–peptidyl, O–acyl hydroxamates: comparison of the selective inhibition of serine and cysteine proteinases. Biochim Biophys Acta 1295: 179–186.

Doman RK, Perez M, Donato NJ (1999). JNK and p53 stress signaling cascades are altered in MCF–7 cells resistant to tumor necrosis factor–mediated apoptosis. J. Interferon Cytokine Res 19: 261 – 269.

Duffy MJ (1992). The role of proteolytic enzymes in cancer invasion and metastasis. Clin Exp Metastasis 10: 145–155.

Fearnhead HO, Dinsdale D, Cohen GM (1995). An interleukin–1 beta–converting enzyme–like protease is a common mediator of apoptosis in thymocytes. FEBS Lett 375: 283–288.

Friedrich B, Jung K, Lein M, Turk I, Rudolph B, Mampel G, Schnorr D, and Loening SA (1999). Cathepsin B,H, L and cysteine protease inhibitors in malignant prostate cell lines, primary cultured prostatic cells and prostatic tissue. Eur J Cancer 35: 138–144.

Garcia–Calvo M, Peterson EP, Leiting B, Ruel R, Nicholson DW, Thornberry NA (1998). Inhibition of human caspases by peptide–based and macromolecular inhibitors. J Biol Chem 273: 32608–32613.

Green DR, Reed JC (1998). Mitochondria and apoptosis. Science 281: 1309–1312.

(List continued on next page.)

Primary Examiner—Kenneth R. Horlick
Assistant Examiner—Teresa Strzelecka
(74) Attorney, Agent, or Firm—Merchant & Gould P.C.

(57) ABSTRACT

Embodiments of the present invention provide methods for inhibiting tumor cell growth, or treating cancer cells, in a subject through the administration of a cathepsin inhibitor or inhibitors. Methods for inhibiting inflammatory disease cells as well as other cathepsin expressing cells in a subject with a cathepsin inhibitor or inhibitors are also within the present invention. Furthermore, the present invention relates to inducing cytotoxicity or apoptosis in cells by administering a cytotoxic or an apoptotic dose of a cathepsin inhibitor or inhibitors to the cell. Finally, the present invention relates to the administering of cathepsin expressing vectors to tumor cells so as to inhibit the tumor cells growth.

8 Claims, 6 Drawing Sheets

OTHER PUBLICATIONS

Guitiérrez MI, Cherney B, Hussain A, Mostowski H, Tosato G, Magrath I, Bhatia K (1999). Bax is frequently compromised in Burkitt's lymphomas with irreversible resistance to Fas–induced apoptosis. *Cancer Res* 59: 696–703.

Heidtmann HH, Salge U, Abrahamson M, Bencina M, Kastalic L, Kopitar–Jerala N, Turk V, and Lah TT (1997). Cathepsin B and cysteine protease inhibitors in human lung cancer cell lines. *Clin Exp Metastasis* 15: 368–381.

Henkart PA (1996). ICE family protease: mediators of all apoptotic death? *Immunity* 4: 195–201.

Isahara K, Ohsawa Y, Kanamori S, Shibata M, Waguri S, Sato N, Gotow T, Watanabe T, Momoi T, Urase K, Kominami E, and Uchiyama Y (1999). Regulation of a novel pathway for cell death by lysosomal aspartic and cysteine proteases. *Neuroscience* 91: 233–249.

Jones B, Roberts PJ, Faubion WA, Kominami E, and Gores GJ (1998). Cystatin A expression reduces bile salt – induced apoptosis in a rat hepatoma cell line. *Am J Physiol* 275: G723–730.

Keppler D, Sameni M, Moin K, Mikkelsen T, Diglio C, and Sloane B (1996). Tumor progression and angiogenesis: cathepsin B & Co. *Biochem Cell Biol* 74: 799–810.

Kos J. and Lah TT (1998). Cysteine proteinase and their endogenous inhibitors: Target proteins for prognosis, diagnosis and therapy in cancer (Review). *Oncol Rep* 5: 1349–1361.

Li P, Nijhawan D, Budihardjo I, Srinivasula SM, Ahmad M, Alnemri E, Wang X (1997). Cytochrome c and dATP–dependent formation of Apaf–1/caspase–9 complex initiates an apoptotic protease cascade. *Cell* 91: 479–489.

Lowe SW, Ruley HE, Jacks T, Housman DE (1993). p53–dependent apoptosis modulates the cytotoxicity of anticancer agents. Cell 74: 957–967.

Lowe SW, Schmitt EM, Smith SW, Osborne BA, Jacks T (1993b). p53 is required for radiation–induced apoptosis in mouse thymocytes. Nature 362: 847–849.

Magi–Galluzzi C, Montironi R, Cangi MG, Wishnow K, Loda M (1998). Mitogen–activated protein kinases and apoptosis in PIN. *Virchows Arch* 432: 407–413.

Makarewicz R, Drewa G, Szymanski W, and Skonieczna–Makarewicz I (1995). Cathepsin B in predicting the extent of the cervix carcinoma. *Neoplasma* 42: 21–24.

Meijerink JP, Mensink EJ, Wang K, Sedlak TW, Sloetjes AW, de Witte T, Waksman G, Korsmeyer SJ (1998). Hematopoietic malignancies demonstrate loss–of–function mutations of BAX. *Blood* 91: 2991–2997.

Memon SA, Moreno MB, Petrak D, Zacharchuk CM (1995). Bcl–2 blocks glucocorticoid—but not as Fas—or activation–induced apoptosis in a T cell hybridoma. *J Immunol* 155: 4644–4652.

Mort JS, and Buttle DJ. Cathepsin B (1997). *Int J Biochem Cell Biol* 29: 715–720.

Peller S (1998). Clinical implications of p53: effect on prognosis, tumor progression and chemotherapy response. Cancer Biol. 8: 379–387.

Pronk GJ, Ramer K, Amiri P, Williams LT (1996). Requirement of an ICE–like protease for induction of apoptosis and ceramide generation by REAPER. *Science* 271: 808–810.

Roberts LR, Kurosawa H, Bronk SF, Fesmier PJ, Agellon LB, Leung W–Y, Mao F, and Gores GJ (1997). *Gastroenterology* 113: 1714–1726.

Rooprai HK, and McCormick D (1997). Proteases and their inhibitors in human brain tumors: a review. *Anticancer Res* 17: 4151–4162.

Sameni M, Elliott E, Ziegler G, Fortgens PH, Dennison C and Sloane BF (1995). Cathepsin B and cathepsin D are localized at the surface of human breast cancer cells. *Pathol Oncol Res* 1: 43–53.

Schlegel J, Peters I, Orrenius S, Miller DK, Thormberry NA, Yamin TT, Nicholson DW (1996). CPP32/apopain is a key interleukin 1 beta converting enzyme–like protease involved in Fas–mediated apoptosis. *J Biol Chem* 271: 1841–1844.

Shibata M, Kanamori S, Isahara K, Ohsawa Y, Konishi A, Kametaka S, Watanabe T, Ebisu S, Ishido K, Kominami E, and Uchiyama Y (1998). Participation of cathepsins B and D in apoptosis of PC12 cells following serum deprivation. *Biochem Biophys Res Commun* 251: 199–203.

Slee EA, Zhu H, Chow SC, MacFarlane M, Nicholson DW, Cohen GM (1996. Benzyloxycarbonyl–Val–Ala–Asp (OMe) fluoromethylketone (Z–VAD.FMK) inhibits apoptosis by blocking the processing of CPP32. *Biochem J* 315: 21–24.

Sloane BF, Moin F, Sameni M, Tait LR, Rozhin J, and Ziegler G (1994). Membrane–association of cathepsin B can be induced by transfection of human breast cells with eHa–ras oncogene. *J Cell Sci* 107: 373–384.

Strohmaier AR, Porwol T, Acker H, and Spiess E (1997). Tomography of cells by confocal laser scanning microscopy and computer–assisted three–dimensional image resonstruction: localization of cathepsin B in tumor cells penetrating collagen gels in vitro. *J Histochem Cytochem* 45: 975–983.

Thornberry NA, Lazebnik Y (1998). Caspases: enemies within. *Science* 281: 1312–1316.

Uckun FM, Waddick KG, Mahajan S, Xiao J, Takata M, Bolen J, Kurosaki T (1996). BTK is a mediator of radiation–induced apoptosis in DT–40 lymphoma B cells. *Science* 273: 1096–1100.

Vasilakos JP, Ghayur T, Carroll RT, Giegel DA, Saunders JM, Quintal L, Keane KM, Shivers BD (1995). IL–1 beta converting enzyme (ICE) is not required for apoptosis induced by lumphokine deprivation in an IL–2 dependent T cell line. *J Immunol* 155(7): 3433–3442.

Weiss RE, Liu BC, Ahlering T, and Dubeau MJ (1990). Mechanism of human bladder tumor invasion: role of protease cathepsin B. *J Urol* 144: 798–804.

Xia Z, Dickens M, Raingeaud J, Davis RJ, Greenberg ME (1995). Opposing effects of ERK and JNK–p38 MAP kinases on apoptosis. *Science* 270: 1326–1331.

Yan S, Sameni M. and Sloane BF (1998). Cathepsin B and human tumor progression. *Biol Chem* 379: 113–123.

Zhu D–M, Fang W–H, Narla R–K, and Uckun FM (1999). A requirement for protein kinase C inhibition for calcium–triggered apoptosis in Acute lymphoblastic leukemia cells. *Clin Can Res* 5: 355–360.

Zuo H, Henzel WJ, Liu X, Lutschg A, Wang X (1997). Apaf–1, a human protein homologous to C. elegans CED–4, participates in cytochrome c–dependent activation of caspase–3. *Cell* 90: 405–413.

Baldwin E, Bhat T, Gulnik S, Hosur M, Sowder II R, Cachau R, Collins J., Silva A, (1993). Crystal structures of native and inhibited forms of human cathepsin D: Implications for lysosomal targeting and drug design. *Proc. Natl. Acad. Sci.* 90: 6796–6800.

Mizuochi T, Yee S–T, Kasai M, Kakiuchi T, Muno D, Kominami E (1994). Both cathepsin B and cathepsin D are necessary for processing of ovalbumin as well as fo rdegradation of class II MHC invariant chain. *Immunol. Lett.,* 43: 189–193.

Keyszer G, Herr A, Kriegsmann J, Geiler T, Trabandt A, Keysser M, Gay R, Gay S, (1995). Comparative Analysis of Cathepsin L, Cathepsin D, and Collagenase Messenger RNA Expression in Synovial Tissues of patients with rheumatoid arthritis and osteoarthritis, by in Situ Hybridization. *Arthritis Rheum.,* 38: 976–984.

Wyllie A, Kerr J, Currie A (1980) Cell Death: The Significance of Apoptosis. *Int. Rev. Cytol.,* 68: 251–306.

Summers M, Smith G (1987). A Manual of Methods for Baculovirus Vectors and Insect Cell Culture Procedures. *Texas Agriculture Experiment Station Bulletin,* 1555.

Kao F, Puck T. (1968). Genetics of Somatic Mammalian Cells, VII. Induction and Isolation of Nutritional Mutants in Chinese Hamster Cells. *Proc. Natl. Acad. Sci. USA,* 60, 1275–1281.

Myers D, Jun X, Waddick K, Forsyth C, Chelstrom L, Gunther R, Tumer N, Bolen J, Uckun F. (1995). Membrane–associated CD19–LYN complex is an endogenous p53–independent and Bcl–2–independent regulator of apoptosis in human B–lineage lymphoma cells. *Proc. Natl. Acad. Sci. USA,* 92: 9575–9579.

Graham F, Prevec L, (1991). Manipulation of Adenovirus Vectors. *Gene Transfer and Expression Protocols,* pp. 109–128.

Graham F, Van Der Eb A (1973). A New Technique for the Assay of Infectivity of Human Adenovirus 5 DNA. *Virology,* 52, 456–457.

Chisholm V., (1995). High efficiency gene transfer into mammalian cells. *DNA Cloning IV: A Practical Approach, Mammalian Systems,* Glover and Hanes, eds., pp 1–41.

Andreason G. (1993) Electroporation Asa Technique for the Transfer of Macromolecules into Mammalian Cell Lines. *J. Tiss. Cult. Meth.,* 15, 56–62.

* cited by examiner

CATHEPSIN INHIBITORS IN CANCER TREATMENT

FIELD OF THE INVENTION

This invention relates to inhibition of cysteine cathepsins for treating cancer and other human disease states. More particularly the invention relates to the induction of apoptotis cell death in human cancer cells by inhibitors of cysteine cathepsins.

BACKGROUND OF THE INVENTION

Cathepsins (Cats) belong to the papain superfamily of lysosomal cysteine proteases. Cathepsins are involved in the normal proteolysis and turnover of target proteins and tissues as well as in initiating proteolytic cascades by proenzyme activation and in participating in MHC class II molecule expression. Baldwin (1993) Proc. Natl. Acad. Sci., 90: 6796–6800; Mixuochi (1994) Immunol. Lett., 43:189–193.

However, aberrant cathepsin expression has also been implicated in several serious human disease states. Cathepsins have been shown to be abundantly expressed in cancer cells, including breast, lung, prostate, glioblastoma and head/neck cancer cells, (Kos et al. (1998) Oncol. Rep., 5:1349–1361; Yan et al. (1998) Biol. Chem., 379:113–123; Mort et al. (1997) Int. J Biochem. Cell Biol., 29: 715–720; Friedrick et al. (1999) Eur. J Cancer, 35:138–144) and are associated with poor treatment outcome of patients with breast cancer, lung cancer, brain tumor and head/neck cancer. Kos et al, supra. Additionally, aberrant expression of cathepsin is evident in several inflammatory disease states, including rheumatoid arthritis and osteoarthritis. Keyszer (1995) Arthritis Rheum., 38:976–984.

The molecular mechanisms of cathepsin activity are not completely understood. Recently, it was shown that forced expression of cathepsin B rescued cells from serum deprivation-induced apoptotic death (Shibata et al. (1998) Biochem. Biophys. Res. Commun., 251: 199–203) and that treatment of cells with antisense oligonucleotides of cathepsin B induced apoptosis. Isahara et at. (1999) Neuroscience, 91:233–249. These reports suggest an antiapoptotic role for the cathepsins that is contrary to earlier reports that cathepsins are mediators of apoptosis. Roberts et al (1997) Gastroenterology, 113: 1714–1726; Jones et al. (1998) Am. J Physiol., 275: G723–730.

Cathepsin inhibitor I Z-Phe-Gly-NHO-Bz (CATI-1) is a selective inhibitor of cathepsin activity. Demuth et al. (1996) Biochem. Biophy. Acta, 1295: 179–186. Little is known on the significance of cathepsin inhibition, especially in the fields of biomedical research and therapeutic drug design. Against this backdrop the present invention has been developed.

SUMMARY OF THE INVENTION

The present invention involves the surprising and unexpected discovery that cathepsin inhibitors and methods of use for cathepsin inhibitors trigger cathepsin dependent apoptosis in cancer cells and in cells having aberrant levels of cathepsin.

One aspect of the present invention is a method for inhibiting the growth of tumor cells in a subject by administering to the subject a cathepsin inhibitor. The method can include inducing the tumor cells to become apoptotic.

Another aspect of the invention is a method of treating cancer cells in a subject by administering a therapeutically effective amount of cathepsin inhibitor to the subject. The cancer cells can be solid cancer cells, for example breast cancer and prostate cancer cells, or can be cancer of the white blood cells, for example leukemia.

Another aspect of the invention is a method for inhibiting inflammatory disease in a subject by administering to the subject a cathepsin inhibitor. The inflammatory disease can be rheumatoid arthritis.

Another aspect of the invention is a method for inducing cytotoxicity in a cell by administering a cytotoxic dose of cathepsin inhibitor to the cell.

Another aspect of the invention is a pharmaceutical composition having a substantially purified cathepsin inhibitor and a pharmaceutically acceptable carrier.

Another aspect of the invention is a method for inhibiting growth of a tumor cell by making a recombinant vector that expresses a cathepsin inhibitor and administering the recombinant vector to the tumor cell.

Finally, another aspect of the invention is a method for inducing apoptosis in a cell by expressing a heterologous nucleic acid sequence encoding the cathepsin inhibitory peptide in a host cell having enhanced cathepsin activity as compared to control host cells.

DETAILED DESCRIPTION OF THE PREFERRED EMBODIMENT

Definitions

Figure 1:
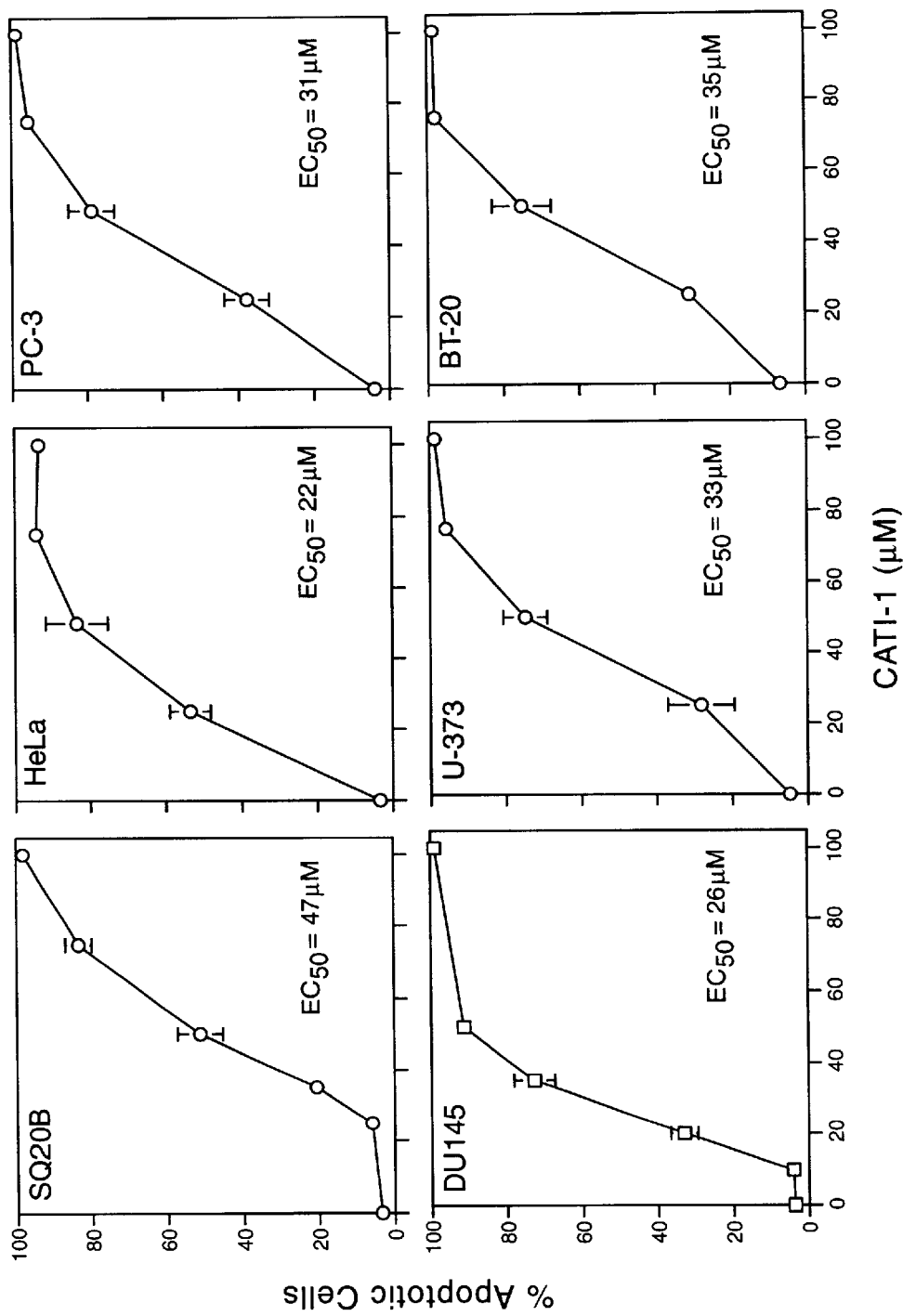
FIG. 1 shows the % apoptosis of SQ-20B, HeLa, PC-3, DU145, U-373 and BT-20 cells treated with CATI-1 at the indicated concentrations (0 to 100 $\mu$M) where % apoptosis represents the total percentage of apoptotic cells at early and advanced stages of apoptosis. Data represents the mean value (±SEM) from 3–5 independent experiments.

The following definitions are provided to facilitate understanding of certain terms used frequently herein and are not meant to limit the scope of the present disclosure.

The term "apoptosis" refers to the genetically programmed process of cell death characterized by cell membrane blebbing, cytoplasmic shrinkage, nuclear chromatin condensation and DNA fragmentation. Wyllie (1990) Int. Rev. Cytol., 68: 251–306. Apoptotic regulatory genes include the p53 tumor suppresser gene, the Bcl-2 gene family, and the caspase family of genes.

The term cell line, host cell or host cells refers to cells established in ex vivo culture. It is a characteristic of host cells discussed in the present disclosure that they be capable of expressing cathepsin and cathepsin inhibitors. Examples of suitable host cells useful for aspects of the present invention include insect and mammalian cells. Specific examples of such cells include SF9 insect cells (Summers and Smith (1987) Texas Agriculture Experiment Station Bulletin, 1555), human primary embyonal kidney cells (293 cells), Chinese hamster ovary (CHO) cells (Puck et al. (1958) Proc. Natl. Acad. Sci. USA, 60, 1275–1281), human cervical carcinoma cells (HELA) (ATCC CCL 2), human squamous cell carcinoma (SQ20B), human breast cancer cells (BT-20), glioblastoma cells (U373), a highly radiation-resistant MILL-AF4 fusion transcript positive t(4;11) pre-pre B ALL cell line (RS4;11), a multidrug resistant BCR-ABL fusion transcript positive t(9;22) pro-B ALL cell line (ALL-1); a highly radiation-resistant and p53 deficient Burkitt's lymphoma cell line (RAMOS) (Myers et al. (1995) Proc. Natl. Acad. Sci. USA, 92: 9575–9579); a Burkitt's leukemia/lymphoma cell line (DAUDI); T-lineage ALL/NHL cells (JURKAT and MOLT-3); a pre-B ALL cell line (NALM-6); etc.

The terms "cancer" and "cancerous" refer to or describe the physiologic condition in mammals that is typically characterized by the loss of responsiveness to normal growth controls. Examples of cancer include but are not limited to, carcinoma, lymphoma, blastoma, sarcoma and leukemia. Cancers can originate from among other things epithelial cells like a carcinoma, or can originate from mesenchymal cells like cancers of the blood cells. Examples of carcinomas include but are not limited to squamous cell, adenocarcinoma and melanoma and examples of cancers of the blood cells are leukemia and lymphoma. For purposes of this disclosure, solid tumors are tumors that are not of blood cell origin.

The term cathepsin inhibitor refers to chemical compositions, polypeptides, polynucleotides, etc. that inhibit the enzymatic activity of cathepsin family members. One example of a cathepsin inhibitor useful in the present invention is cathepsin inhibitor I Z-Phe-Gly-NHO-Bz (CATI-1). Demuth et al. (1996) Biochim. Biophys. Acta., 1295:179–186. CATI-1 can be purchased from Calbiochem, La Jolla, Calif.

As used herein, "cDNA" refers to recombinant DNA formed from the mRNA of the target protein, in the case of the present invention the cDNA can be derived from a calpain inhibitor mRNA. cDNA molecules can be inserted into vectors that favor their expression in target host cells.

As used herein, "control host cell" refers to a cell that has been cultured in parallel with a cell treated under the specified experimental condition, but unlike the treated cell, the host cell has not undergone the specified experimental condition. Control cells represent a baseline from which comparisons are made.

The term inflammatory disease or disorder refers to a fundamental pathogenic process consisting of a dynamic complex of cytologic and histologic reactions that occur in the affected blood vessels and adjacent tissues in response to an injury or abnormal stimulation caused by physical, chemical, or biologic agent. Examples of inflammatory disease within the context of the present invention include, rheumatoid arthritis, osteoarthritis, etc.

The term "nucleic acid sequence" refers to the order or sequence of deoxyribonucleotides along a strand of deoxyribonucleic acid. The order of these deoxyribonucleotides determines the order of amino acids along the polypeptide chain. The deoxyribonucleotide sequence thus codes for the amino acid sequence.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to induce apoptosis of leukemia or breast tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

The term "polynucleotide" refers to a linear sequence of nucleotides. The nucleotides are either a linear sequence of polyribonucleotides or polydeoxyribonucleotides, or a mixture of both. Examples of polynucleotides in the context of the present invention include—single and double stranded DNA, single and double stranded RNA, and hybrid molecules that have both mixtures of single and double stranded DNA and RNA. Further, the polynucleotides of the present invention may have one or more modified nucleotides.

The term "subject" in the context of this invention means a mammal, i.e., any class of higher vertebrates that nourish their young with milk secreted by mammary glands.

The term "treating" or "treatment" in the context of this invention means the prevention or reduction of severity symptoms or effect of a pathological condition, including prolonging life expectancy. In the context of cancer therapy, treatment can include: prevention of tumor growth, reduction of tumor size, enhanced tumor cell death, or increased apoptosis in the tumor.

The term "tumor cell" within the context of the present invention is used synonymously with cancer cell and means a cell that has lost, in some manner, its ability to respond to normal growth signals, i.e., is undergoing abnormally regulated growth.

The term vector, extra-chromosomal vector or expression vector refers to a first piece of DNA, usually double-stranded, which may have inserted into it a second piece of DNA, for example a piece of foreign DNA like the cDNA of CATI-1. Foreign DNA is defined as heterologous DNA, which is DNA that may or may not be naturally found in the host cell and includes additional copies of nucleic acid sequences naturally present in the host genome. The vector transports the foreign DNA into a suitable host cell. Once in the host cell the vector may be capable of integrating into the host cell chromosomes. The vector may also contain the necessary elements to select cells containing the integrated DNA as well as elements to promote transcription of mRNA from the transfected DNA. Examples of vectors within the scope of the present invention include, but are not limited to, plasmids, bacteriophages, cosmids, retroviruses, and artificial chromosomes.

Modes for Carrying out the Invention

The present invention includes novel and unexpected methods of use for cathepsin inhibitors in the selective triggering of cathepsin dependent apoptosis in cancer cells and in cells having aberrant levels of cathepsin. CATI-1, as well as other cathepsin inhibitors, may be useful agents, alone or in combination, in the treatment of cancer, for example to inhibit tumor growth or to kill tumor cells. Cathepsin inhibitors may also be of use in the treatment of inflammatory disease or any other disease state where the target cells show aberrant cathepsin expression.

Within this application, unless otherwise stated, the techniques utilized may be found in any of several well-known references such as: *Molecular Cloning: A Laboratory Manual* (Sambrook et al. (1989) Molecular cloning: A Laboratory Manual), *Gene Expression Technology* (Methods in Enzymology, Vol. 185, edited by D. Goeddel, 1991 Academic Press, San Diego, Calif.), "Guide to Protein Purification" in *Methods in Enzymology* (M. P. Deutshcer, 3d., (1990) Academic Press, Inc.), *PCR Protocols: A Guide to Methods and Applications* (Innis et al. (1990) Academic Press, San Diego, Calif.), Culture of Animal Cells: A Manual of Basic Technique, $2^{nd}$ ed. (R. I. Freshney (1987) Liss, Inc., New York, N.Y.), and *Gene Transfer and Expression Protocols,* pp 109–128, ed. E. J. Murray, The Humana Press Inc., Clifton, N.J.).

Cytotoxic Compounds

The cathepsin inhibitors of the invention are effective cytotoxic agents, for example, against tumor cells such as leukemia and breast cancer cells. In the methods of the invention, the cytotoxic effects of cathepsin inhibitors are achieved by treating, such as tumor cells, with micromolar amounts of the inhibitory compound. By way of example, a particularly useful anti-tumor agent is CATI-1 as shown in the Examples below. Additionally, it is within the scope of the present invention to use one or more cathepsin inhibitors at the same time as cytotoxic agents.

The present invention also includes polynucleotide fragments, analogs and derivatives of CATI-1 sequence (Demuth et al. (1996) Biochim. Biophys. Acta., 1295:179–186) as used as cytotoxic compounds. A fragment, analog or derivative may be made by mutagenesis techniques or other methods known to the art. Additionally, the polynucleotide fragments, analogs and derivatives may include substitutions, deletions or additions that involve one or more nucleotides.

Another embodiment of the present invention are polynucleotides that are at least 75% identical to the polynucleotide sequence for CATI-1 as used as cytotoxic compounds. Further, preferred embodiments are between 80 and 95% identical to the CATI-1 cDNA and highly preferred embodiments are between 95 and 99% identical.

Tumor Treatment

The cathepsin inhibitors of the invention can also be used in methods of tumor treatment, for example, by administering to a subject a cathepsin inhibitor or inhibitors of the invention in order to achieve an inhibition of tumor cell growth, a killing of tumor cells, induced apoptosis, and/or increased patient survival time.

The present invention also includes polynucleotide fragments, analogs and derivatives of the CATI-1 sequence (Demuth et al. (1996) Biochim. Biophys. Acta., 1295:179–186) as used in tumor treatment. A fragment, analog or derivative may be made by mutagenesis techniques or other methods known to the art. Additionally, the polynucleotide fragments, analogs and derivatives may include substitutions, deletions or additions that involve one or more nucleotides.

Another embodiment of the present invention are polynucleotides that are at least 75% identical to the polynucleotide sequence for CATI-1 as used in tumor treatment. Further, preferred embodiments are between 80 and 95% identical to the CATI-1 cDNA and highly preferred embodiments are between 95 and 99% identical.

The cathepsin inhibitors of the invention are suitable for use in mammals. As used herein, "mammals" means any class of higher vertebrates that nourish their young with milk secreted by mammary glands, including, for example, humans, rabbits, and monkeys.

Administration Methods

The cathepsin inhibitors of the present invention can be formulated as pharmaceutical compositions and administered to a mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

The cathepsin inhibitors can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleageous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes. More preferably, the compounds of the present invention are administered parenterally, i.e., intravenously or intraperitoneally, by infusion or injection. In one embodiment of the invention, the compounds may be administered directly to a tumor by tumor injection; or by systemic delivery by intravenous injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms. The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Vectors and Host Cells

In another aspect of the present invention, novel polynucleotides substantially similar to the CATI-1 polynucleotide sequence are subcloned into an extra-chromosomal vector. The subcloned polynucleotide(s) may be joined to a vector having a cis-acting or regulatory element for increased propagation in a host cell (note that the trans-acting factors involved are supplied to the host, supplied by a second vector or supplied by the vector itself upon introduction into the host). This aspect of the invention allows for the in vivo and in vitro expression of the CATI-1 polynucleotide, thus permitting an analysis of cathepsin activity and function. Several vectors that can be used in the context of this invention include: PcDNA3 vector (Invitrogen), vectors having the T3 and T7 polymerase promoters, vectors having the SV40 promoter or the CMV promoter, or any other promoter that either can direct expression of a polypeptide off a polynucleotide, or that one wishes to test for the ability to direct expression of a polypeptide off a polynucleotide.

The present invention also includes polynucleotide fragments, analogs and derivatives of the CATI-1 sequence (Demuth et al. (1996) Biochim. Biophys. Acta., 1295:179–186) that are subcloned into extra-chromosomal vectors. A fragment, analog or derivative may be made by mutagenesis techniques or other methods known to the art. Additionally, the polynucleotide fragments, analogs and derivatives may include substitutions, deletions or additions that involve one or more nucleotides.

Another embodiment of the present invention are polynucleotides that are at least 75% identical to the polynucleotide sequence for CATI-1 as subcloned into extra-chromosomal vectors. Further, preferred embodiments are between 80 and 95% identical to the CATI-1 cDNA and highly preferred embodiments are between 95 and 99% identical.

In a further aspect of the present invention, host cells can be genetically engineered to incorporate the cathepsin inhibitor polynucleotides of the present invention and to express the polypeptides of the present invention. Techniques required for this aspect of the invention are well known in the art (Sambrook et al., Molecular Cloning: A Laboratory Manual, $2^{nd}$ ed., Cold Spring Harbor Press, 1989) and can include calcium phosphate transfection, dextran sulfate transfection, electroporation, lipofection and viral infection (see Graham and van der Eb (1978) Virology, 52, 456–457; Chisholm et al. (1995) DNA Cloning IV: A Practical Approach, Mammalian Systems, Glover and Hanes, eds., pp 1–41; Andreason (1993) J. Tisss. Cult. Meth., 15, 56–62).

The host cells of the present invention may be of any type, including, but limited to, non-eukaryotic and eukaryotic cells. Host cells are cultured using standard tissue culture techniques in conventional media as is well known in the art. The level of expression of the CATI-1 cDNA introduced into a host cell of the invention depends on multiple factors, including gene copy number, efficiency of transcription, messenger RNA processing, stability, and translation efficiency. Accordingly, high level expression of a desired CATI-1 polypeptide according to the present invention will typically involve optimizing one or more of those factors.

EXAMPLES

The following examples are provided to illustrate the invention only, and should not be construed as limiting the scope of the invention.

Example 1

The Cathepsin Inhibitor Z-Phe-Gly-NHO-Bz is Cytotoxic Against Cancer Cells

In vitro clonogenic assays were carried out to determine the cytotoxic activity of the cathepsin inhibitor I (CATI-1) (Z-Phe-Gly-NHO-Bz) against cancer cells. The cancer cell lines used in the assay were U373 (glioblastoma), BT-20 (breast cancer), SQ20B (squamous cell carcinoma), RS4;11 (pro-B ALL), ALL-1 (pre-pre-B ALL), KM-3, MOLT-3 (T-ALL), JURKAT (T-ALL), K-562 (CML), HL-60 (AML), DAUDI (NHL), RAMOS (NHL) and RAJI (NHL). Each cell line was treated under several concentrations of CATI-1 for 24 hours, washed with serum free medium and resuspended in clonogenic medium having 10% fetal bovine serum and 0.9% methylcellulose. Resuspended cells were plated in duplicate 35-mm Petri dishes at 10,000 to 20,000 cells per dish and cultured at 37° C. in a humidified 5% $CO_2$ atmosphere for 5 to 7 days.

Images of colonies in each dish were taken by a digital camera (Princeton Instruments, Inc.) linked to a microscope (Nikon Diaphot 200). Colony numbers were determined using an inverted phase microscope and percent inhibition of colony formation determined using the formula:

% inhibition=(1−(colony number in test sample/colony number in control sample))×100.

Results

As shown in Table 1, cells treated with CATI-1 showed a marked inhibition of clonogenic growth. CATI-1 inhibited colony formation in all tested cell lines, solid and blood cell, in a concentration-dependent fashion with $IC_{50}$ values ranging from 5.5 to 15.4 µM.

This data is a surprising contradiction to the published and expected anti-apoptotic function of cathepsin inhibitors. Roberts et al (1997) Gastroenterology, 113: 1714–1726; Jones et al. (1998) Am. J Physiol., 275: G723–730.

TABLE 1

Inhibition of cancer cell colony formation by CATI-1:

| Cell Line | CATI-1 (uM) | Mean no. of colonies | %, inhibition | $IC_{50}$ (uM) |
|---|---|---|---|---|
| RS4;11 | 0 | 2992 (2412, 3572) | — | 14.6 |
| (pro-B ALL) | 10 | 2676 (2160, 3192) | 10.6 | |
| | 20 | 96 (116, 76) | 96.8 | |
| | 35 | 0 (0, 0) | 100 | |
| ALL-1 | 0 | 1726 (1708, 1744) | — | 6.2 |
| (pre-pre B ALL) | 10 | 338 (348, 328) | 80.4 | |
| | 20 | 7 (6, 8) | 99.6 | |
| | 35 | 0 (0, 0) | 100 | |
| KM-3 | 0 | 2774 (2544, 3004) | — | N.D |
| (pre-B ALL) | 10 | 578 (520, 636) | 79.2 | |
| | 20 | 0 (0, 0) | 100 | |
| MOLT-3 | 0 | 2110 (2060, 2160) | — | 5.5 |
| (T-ALL) | 10 | 194 (124, 264) | 90.8 | |
| | 20 | 18 (16, 20) | 99.1 | |
| | 35 | 0 (0, 0) | 100 | |
| JURKAT | 0 | 5680 (5920, 5440) | — | 14.5 |
| (T-ALL) | 10 | 5110 (5260, 4960) | 10.0 | |
| | 20 | 64 (40, 88) | 98.9 | |
| | 35 | 0 (0, 0) | 100 | |
| K-562 | 0 | 4700 (5256, 4144) | — | 15.4 |
| (CML) | 10 | 3806 (3980, 3632) | 19.0 | |
| | 20 | 1086 (1196, 976) | 76.9 | |
| | 35 | 10 (12, 8) | 99.8 | |
| HL-60 | 0 | 4224 (4220, 42280) | — | N.D |
| (AML) | 10 | 0 (0, 0) | 100 | |
| DAUDI | 0 | 6014 (6100, 5928) | — | N.D |
| (NHL) | 10 | 0 (0, 0) | 100 | |
| RAMOS | 0 | 2726 (2600, 2852) | — | 10.1 |
| (NHL) | 10 | 1442 (1344, 1540) | 47.1 | |
| | 20 | 594 (660, 528) | 78.2 | |
| | 35 | 0 (0, 0) | 100 | |
| RAJI | 0 | 1240 (1196, 1280) | — | 5.8 |
| (NHL) | 10 | 168 (124, 212) | 86.5 | |
| | 20 | 32 (40, 24) | 97.4 | |
| | 35 | 0 (0, 0) | 100 | |
| U373 | 0 | 1664 (1675, 1652) | 0 | N.D |
| (brain tumor) | 30 | 76 (84, 67) | 97 | |
| | 50 | 0 | 100 | |
| BT-20 | 0 | 3656 (3480, 3744) | 0 | N.D |
| (breast cancer) | 50 | 177 (154, 200) | 95 | |
| | 100 | 0 | 100 | |
| SQ20B | 0 | 3072 (2976, 3168) | 0 | N.D |
| (neck cancer) | 50 | 1838 (1732, 1944) | 40 | |
| | 100 | 306 (280, 332) | 90 | |

EXAMPLE II

Cathepsin Inhibitor I Induces Apoptosis in Human Tumor Cell Lines

Quantitative flow cytometric apoptosis detection assays and TUNEL assays were performed to determine if cathepsin inhibitor I treated human tumor cells undergo apoptosis.

Quantitative flow cytometric apoptosis detection assays were performed on BT-20 (breast cancer), PC-3 (prostate cancer), U373 (glioblastoma), SQ20B (squamous cell carcinoma), HeLa (cervix cancer), and DU145 (prostate cancer). Just prior to the assay, one mg/ml stock solutions of MC540 (Sigma, St. Louis, Mo.) and PI (Sigma, St. Louis, Mo.) were filtered through a 0.22 µm filter and stored at 4° C. in the dark. CATI-1 treated cell lines was harvested, and 1×10$^6$ cells suspended and stained with 5 µg/ml MC540 and 10 µg/ml propidium iodide (PI) (Uckun et al. (1996) Science, 273: 1096–1100) at 4° C. in the dark for 24 hours. Stained cells were analyzed with a FACStar Plus flow cytometer (Becton Dickinson, San Jose, Calif.) using the 488-nm excitation from an argon laser. MC540 and PI emissions were split with a 600-nm short pass diachronic mirror; a 575-nm band pass filter was placed in front of one photomultiplier tube to measure MC540 emission, and 635-nm band pass filter was used for PI emission. In each experiment approximately 10,000 cells were analyzed by FACS and the percentage of cells at early (MC540 fluorescence only) and advanced (dual MC540 plus PI fluorescence) stages of apoptosis obtained.

DNA cleavage as an indicator of apoptosis was determined using the in situ terminal deoxynucleotidyl transferase (TdT)-mediated dUTP nick-end-labeling method (TUNEL assay) of Boehringer Mannheim (Cell Death Detection Kit) as described in Zhu et al. (1999) Clin. Can. Res., 5:355–360. Briefly, CATI-1 treated cells and control cells were harvested and resuspended in phosphate-buffered saline (PBS) at a density of 5×10$^6$ cells/ml. Fifty µl of each cell suspension was placed into a PAP Pen (Zymed Laboratories Inc., South San Francisco, Calif.)-circled area on Superfrost/Plus slide (Fisher Scientific, Pittsburgh, Pa.) that was coated for cell adhesion. Cells were allowed to adhere to the slide for 10 minutes, washed with PBS and fixed with a 4% paraformadehyde in PBS solution for 20 minutes. After washing the slides twice with PBS, the cells were permeabilized by treatment with 100 µl of 20 mM SDS in PBS for 10 minutes. Permeabilized cells were washed 3 times with PBS and incubated for one hour at 37° C. with a reaction mixture containing terminal deoxynucleotidyl transferase (TdT) and fluorescein isothiocyanate (FITC)-conjugated digoxigenin-11-UTP for labeling of the exposed 3'-hydroxyl ends of fragmented nuclear DNA. After washing the cells with PBS, a coverslip was mounted onto a slide with PI containing mounting medium (Vector Labs, Bulingame, Calif.). The fluorescent images of the cells were acquired with a confocal laser scanning microscope (MRC 1024, Bio-Rad, Inc., Richmond, Calif.). Apoptotic cells having fragmented DNA incorporate abundant amounts of FITC-labeled dUTP and exhibit a green fluorescence. However, non-apoptotic cells incorporate only insignificant amounts of FITC-labeled dUTP due to the lack of exposed 3'-hydroxyl ends in intact DNA and consequently have much less green fluorescence than apoptotic cells. DNA bound PI emits strong red nuclear fluorescence from all the cells.

Results

Figure 2:
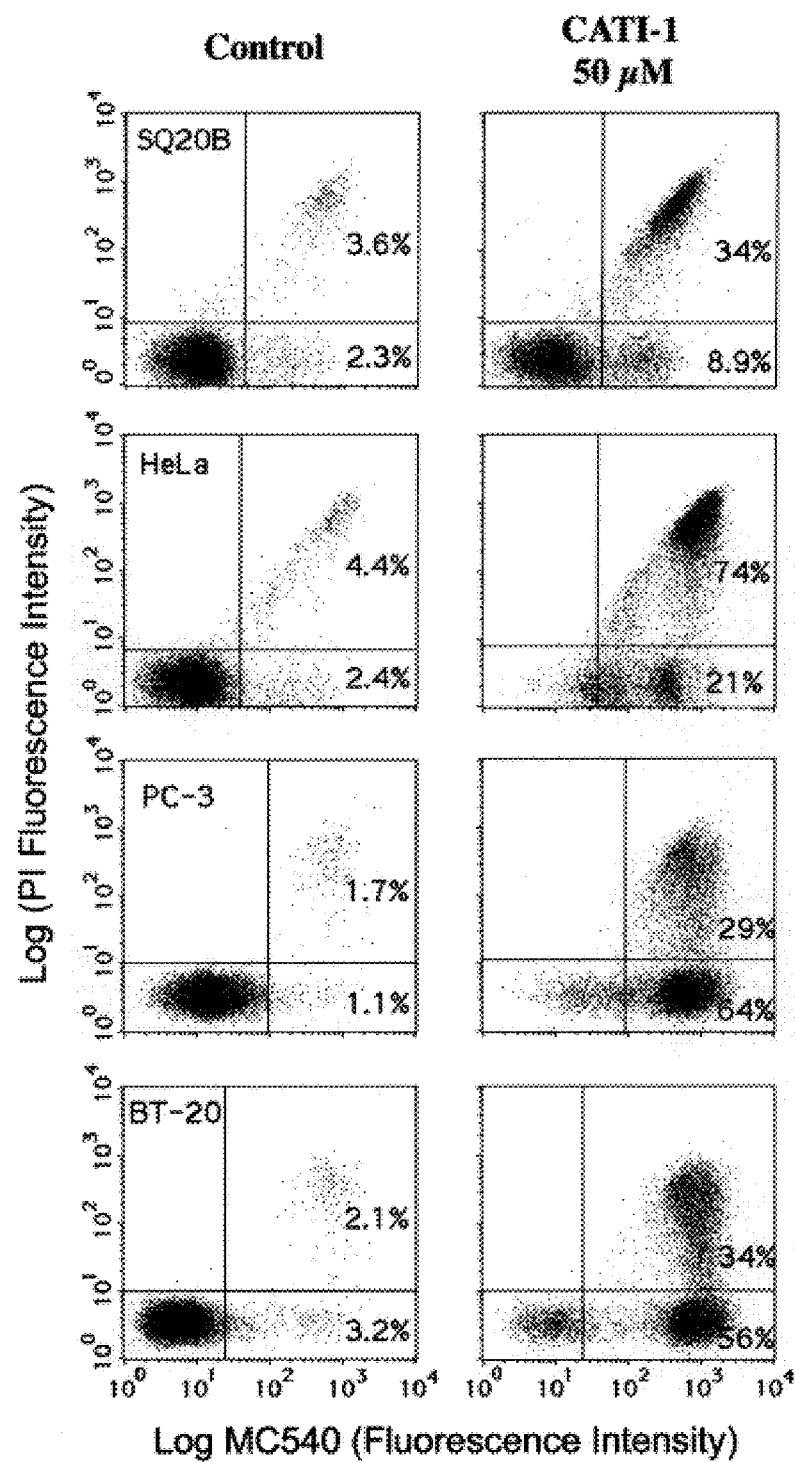
FIG. 2 shows a representative FACS-correlated two color display of CATI-1 treated SQ-20B, HeLa, PC-3 and BT-20 cells. The percentages indicate the fraction of cells at an early stage of apoptosis (lower right quadrant), as measured by single MC540 fluorescence, and the fraction of cells at an advanced stage of apoptosis (upper right quadrant).
Figure 3:
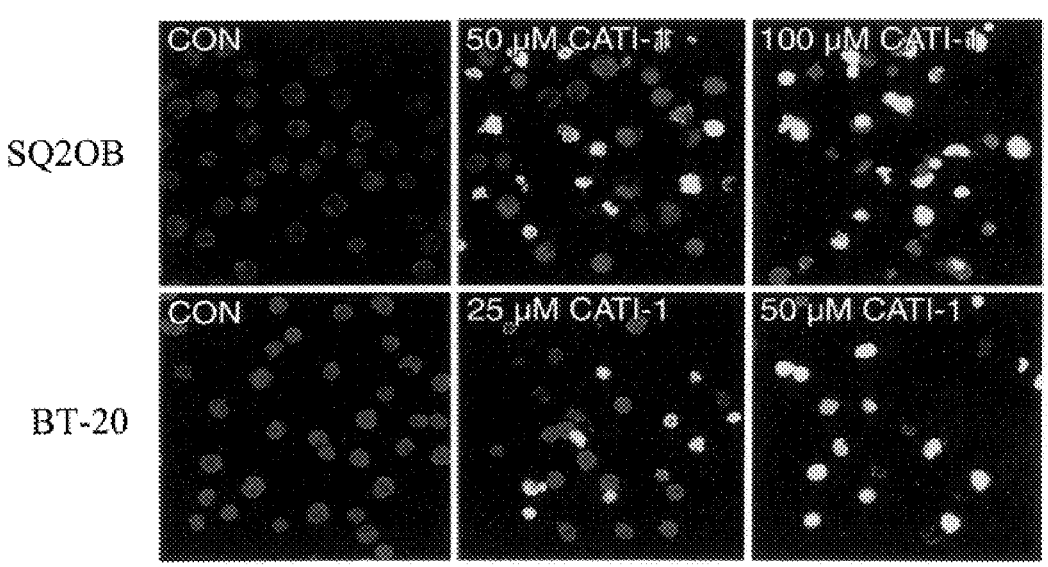
FIGS. 3 shows the characteristic DNA cleavage of apoptosis in 50 $\mu$M and 100 $\mu$M CATI-1 treated cancer cells. Red fluorescence from the PI marks nuclei and yellow/green fluorescence from FITC-conjugated digoxigenin-11-dUTP coupled to 3'-hydroxyl end of DNA fragments indicates apoptotic fragmentation of DNA.

As shown in FIGS. 1—3, exposure to CATI-1 induces apoptosis in BT-20, PC-3, U373, SQ20B, HeLa, and DU145 cells. Data from representative quantitative flow cytometric apoptosis detection assays are illustrated graphically in FIG. 1 where the % of apoptotic cells is plotted against the concentration of CATI-1. Clearly in all the cells tested CATI-1 induced apoptosis.

As shown in FIG. 2, cytometric apoptosis detection assays illustrated that CAPI-1 induced apoptosis on all tested cancer cell lines. Percentages indicate the fraction of cells at an early stage of apoptosis, as measured by single MC540 fluorescence (lower right), and the fraction of cells at an advanced stage of apoptosis, as measured by dual MC540/PI fluorescence (upper right).

Data shown in FIGS. 1 and 2 were confirmed using the TUNEL assay as is illustrated in FIG. 3. CATI-1 treated SQ20B and BT-20 cells showed nuclear green fluorescence consistent with DNA fragmentation and hence apoptosis. Note the lack of fluorescence in the untreated cells (CON) showing that the DNA fragmentation was specific to CATI-1 treatment.

EXAMPLE III

Cathepsin Inhibitor I Induced Apoptosis Is p53-Independent

The materials and methods discussed in Example II were used on several p53 deficient cell lines to examine whether CATI-1 induces apoptosis in a p53-independent manner. Effects of CATI-1 were investigated on a lung squamous carcinoma cell line, NCI-H520 cells, and a chronic myeloid leukemia cell line, K562 cells.

Results

Figure 4A:
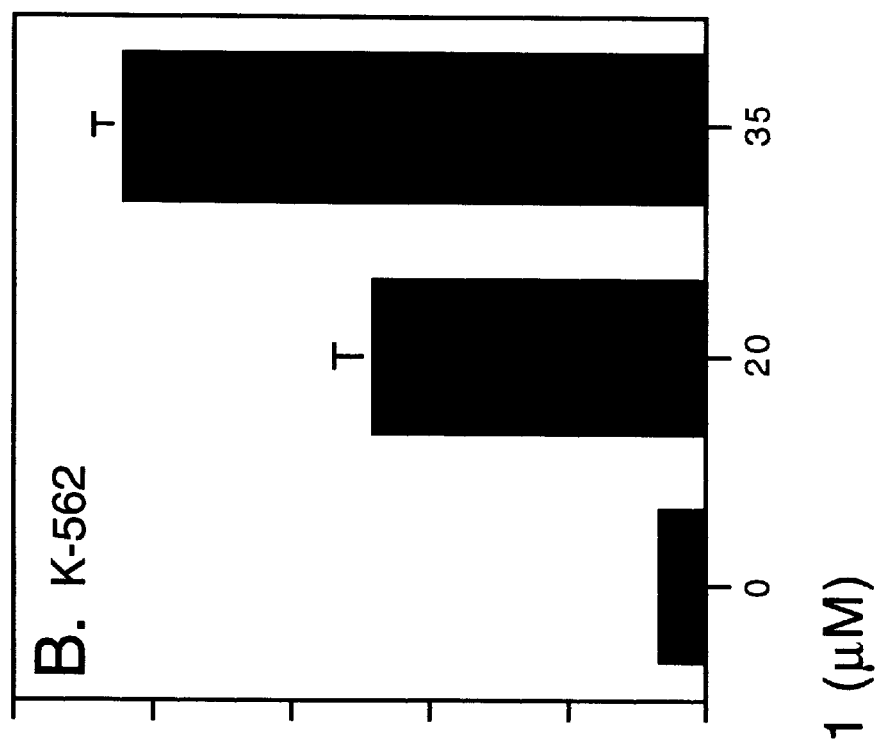
FIGS. 4A and 4B show the % apoptosis in p53 deficient cells, NCI-H520 (A) and K562 (B), treated with CATI-1 where % apoptosis represents the total percentage of apoptotic cells at early and advanced stages of apoptosis. Data represents the mean value (±SEM) from independent experiments.
Figure 4B:
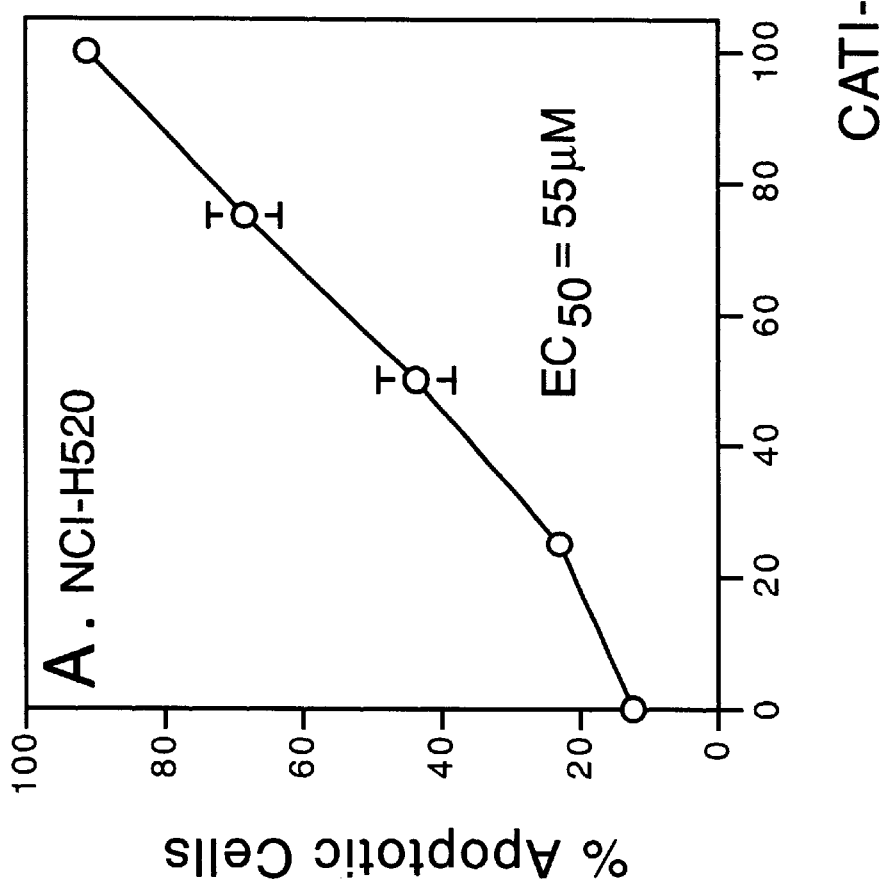

It is generally known that several chemotherapeutic drugs induce apoptosis in human cancer cells in a p53 dependent fashion and that loss of p53 function has been associated with drug resistance. As shown in FIGS. 4A and 4B, CATI-1 acts in a p53 independent manner to induce apoptosis. Results were similar to the results illustrated in FIGS. 1–3 and Table 1 for p53 expressing cell lines. NCI-H520 cells underwent apoptosis with a CATI-1 $EC_{50}$ value of 55 $\mu$M and K-562 showed a CATI-1 $EC_{50}$ value of approximately 20 $\mu$M.

These results are surprising given the central role p53 plays in mediating apoptotic responses. Importantly, CATI-1 treatment can be an effective therapeutic tool against tumor cells that have reduced or abrogated p53 function.

EXAMPLE IV

Cathepsin Inhibitor I Induced Apoptosis Is BAX-Independent

The materials and methods discussed in Examples I and II were used on (1) JURKAT (T-ALL) and KM3 (pre-B-ALL) cell lines that have frameshift mutations of the bax gene that abrogate BAX protein expression (Meijerink et al. (1998) Blood, 91:2991–2997; Brimmell et al. (1998) Oncogene, 16: 1803–1812); (2) DAUDI (Burkitt's lymphoma) cells that have a loss-of function mutation of BAX; and (3) RAJI (Burkitt's lymphoma) cells that show down-regulation of BAX expression and resistance to Fas-mediated apoptosis (Gutiérrez et al. (1999) Cancer Res., 59: 696–703) to determine whether the BAX protein was required for CATI-1 apoptotic activity.

Results

It is generally known that several human hematopoitic malignancies show reduced or abrogated expression of BAX protein. Table 1 shows that all four BAX deficient cell lines were highly susceptible to CATI-1 induced apoptosis. These results demonstrate that BAX is not required for cathepsin inhibitor I induced apoptosis.

Importantly, CATI-1 treatment can be an effective therapeutic tool against tumor cells that have reduced or abrogated BAX function.

EXAMPLE V

Cathepsin Inhibitor I Induced Apoptosis Is Caspase Independent

Human cancer cell lines were treated with 50 $\mu$M CATI-1 in the presence and absence of 50 $\mu$M caspase inhibitor I (Z-Val-Ala-Asp(Ome)-$CH_2$F) (Calbiochem, La Jolla, Calif.) for 24 hours to determine whether caspases were required for cathepsin inhibitor activity. Caspase inhibitor I is a specific and irreversible inhibitor shown to inhibit caspase-mediated apoptosis. Slee et al. (1996) Biochem. J, 315: 21–24; Chow et al. (1995) FEBS Lett., 364: 134–138; Fearnhead et al. (1995) FEBS Lett., 375:283–288; Garcia-Calvo et al. (1998) J Biol. Chem., 273: 32608–32613. Quantitative flow cytometric apoptosis detection assays were performed on treated cells as previously discussed in Example II.

Results

Figure 5:
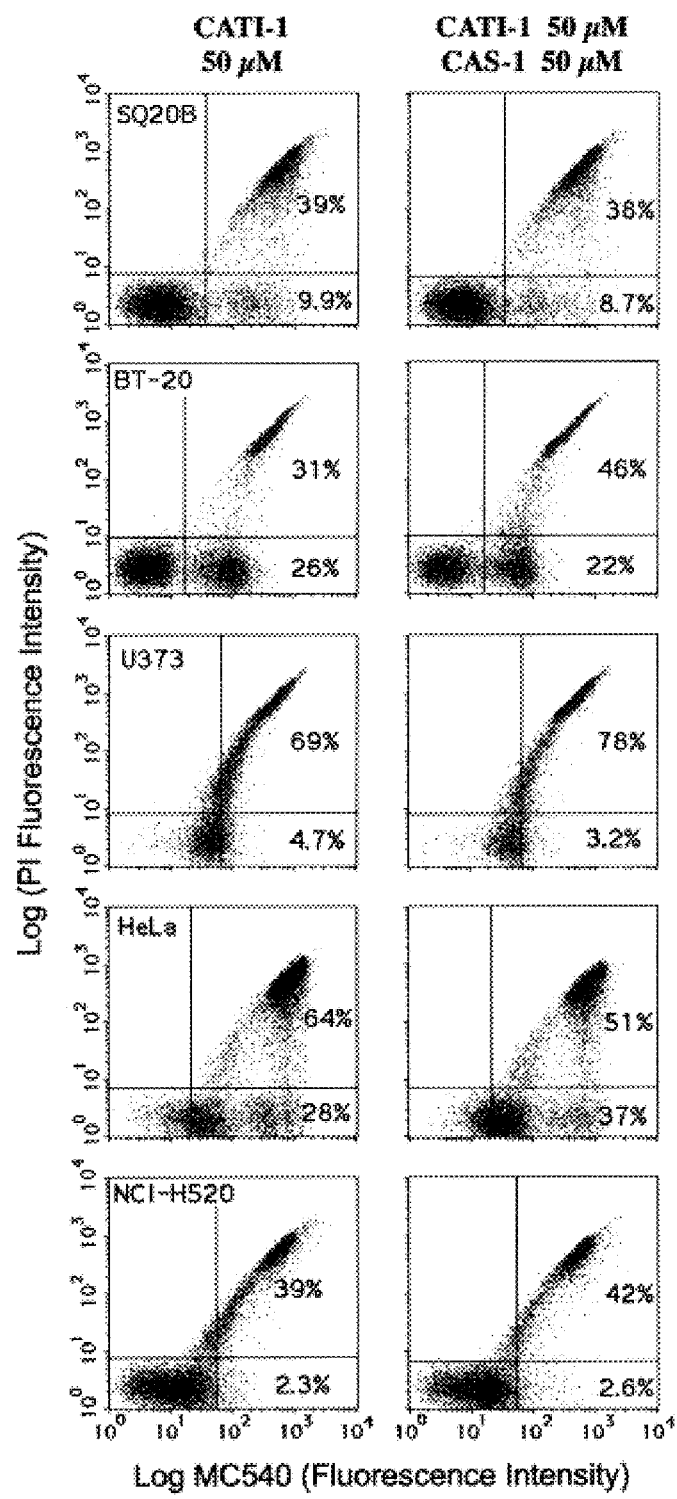
FIG. 5 shows a representative FACS-correlated two color display of CATI-1 treated SQ-20B, BT-20, U373, HeLa and NCI-H520 cells in the presence and absence of 50 $\mu$M caspase inhibitor I treatment. The percentages indicate the fraction of cells at an early stage of apoptosis (lower right quadrant), as measured by single MC540 fluorescence, and the fraction of cells at an advanced stage of apoptosis (upper right quadrant).

As shown in FIG. 5, caspase inhibitor I had no detectable impact on CATI-1 induced apoptosis on any cell line tested. These results indicate that caspases are not mediators of CATI-1 triggered apoptosis.

As was the case in the p53 example above, caspases are known important regulators of apoptosis. This data is surprising and important in that CATI-1 treatment can be an effective therapeutic tool against tumor cells that have reduced or abrogated caspase function.

EXAMPLE VI

Cathepsin Inhibitor I Induced Apoptosis Is MAP Kinase Independent

SQ20B cells and Hela cells were treated with 0 to 80 $\mu$M CATI-1 for 24 hours in the absence and presence of 20 $\mu$M of the kinase inhibitors SB 202190 and PD 98059 (Calbiochem, La Jolla, Calif.). Quantitative flow cytometric apoptosis detection assays were performed as discussed in Example II on treated cells and data plotted as % apoptosis against CATI-1 concentrations.

Results

Figure 6B:
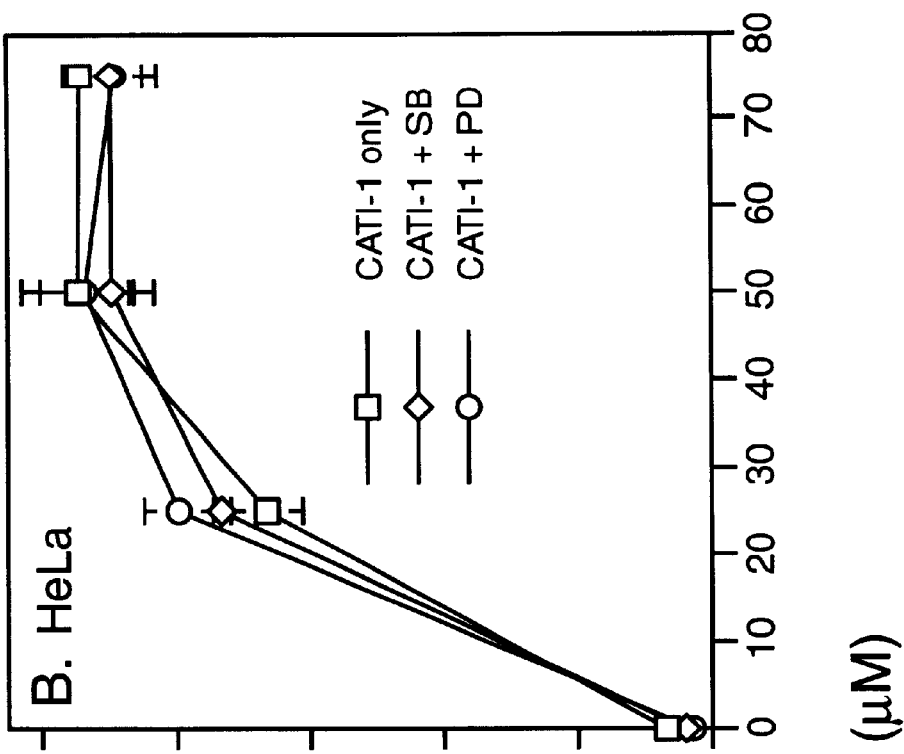
FIGS. 6A and 6B shows apoptosis in MAP kinase inhibited cells, SQ-20B (A) and Hela cells (B), treated with CATI-1. Apoptosis was assayed by flow cytometry and the % apoptosis represents the total percentage (mean±SEM) of apoptotic cells at early and advanced apoptosis stages from 3 independent experiments.
Figure 6A:
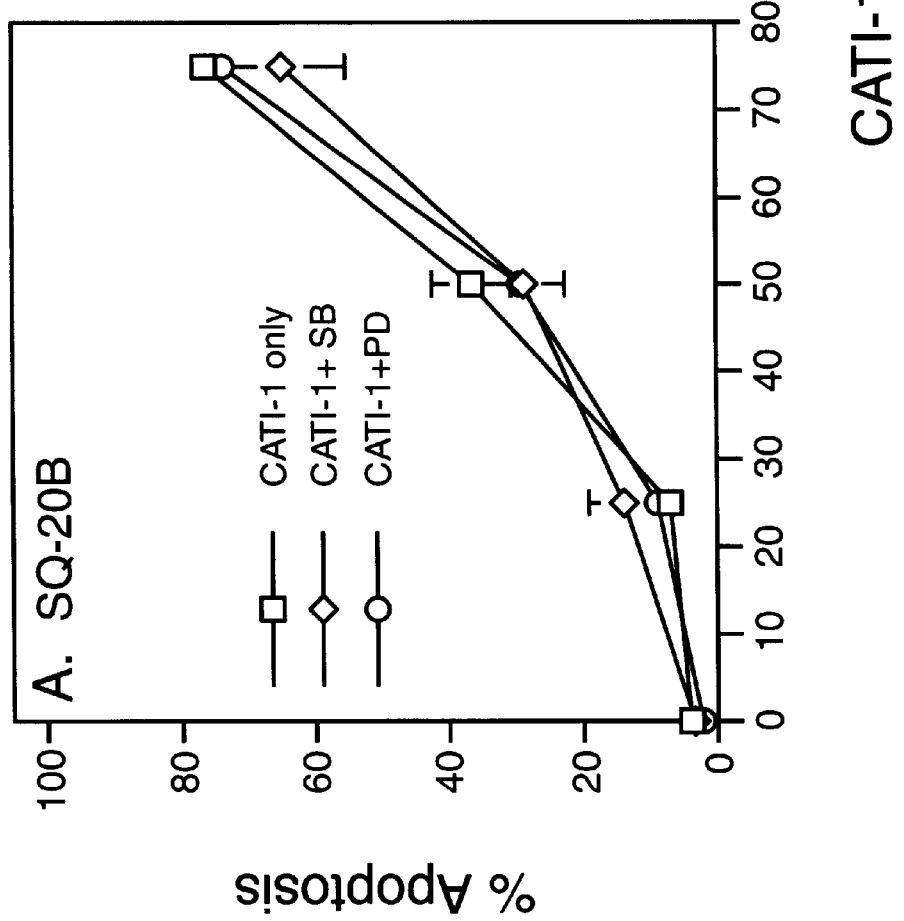

As shown in FIG. 6, kinase inhibitors had no detectable impact on CATI-1 induced apoptosis on any cell line tested. These results indicate that MAP kinases are not mediators of cathepsin inhibitor I triggered apoptosis.

All publications, patents and patent documents described herein are incorporated by reference as if fully set forth. The invention described herein may be modified to include alternative embodiments. All such obvious alternatives are within the spirit and scope of the invention, as claimed below.

REFERENCES

1. Blandino G B, Levine A J, Oren M (1999). Mutant p53 gain of function: differential effects of different p53 mutants on resistance of cultured cells to chemotherapy. Onogene 18: 477–485.
2. Brimmell M, Mendiola R, Mangion J, Packham G (1998). BAX frameshift mutations in cell lines derived from human haemopoietic malignancies are associated with resistance to apoptosis and microsatellite instability. Oncogene 16: 1803–1812.
3. Chow S C, Weiss M, Kass G E, Holmstrom T H, Eriksson J E, Orrenius S (1995). Involvement of multiple proteases during Fas-mediated apoptosis in T lymphocytes. FEBS Lett 364: 134–138.
4. Cordone I, Masi S, Mauro F R, Soddu S, Morsilli O, Valentini T, Vagna M L, Guglielmi C, Mancini F, Guiliacci S, Sacchi A, Mandelli F, Foa R (1998). p53 expressions in B-cell chronic lymphocytic leukemia: a marker of disease progression and poor prognosis. Blood 91: 4342–4349.
5. Demuth H U, Schierhorn A, Bryan P, Hofke R, Kirschke H, and Bromme D (1996). N-peptidyl, O-acyl hydroxamates: comparison of the selective inhibition of serine and cysteine proteinases. *Biochim Biophys Acta* 1295: 179–186.
6. Doman R K, Perez M, Donato N J (1999). JNK and p53 stress signaling cascades are altered in MCF-7 cells resistant to tumor necrosis factor-mediated apoptosis. *J. Interferon Cytokine Res* 19: 261–269.
7. Duffy M J (1992). The role of proteolytic enzymes in cancer invasion and metastasis. *Clin Exp Metastasis* 10: 145–155.
8. Fearnhead H O, Dinsdale D, Cohen G M (1995). An interleukin-1 beta-converting enzyme-like protease is a common mediator of apoptosis in thymocytes. FEBS Lett 375: 283–288.
9. Friedrich B, Jung K, Lein M, Turk I, Rudolph B, Mampel G, Schnorr D, and Loening S A (1999). Cathepsin B, H, L and cysteine protease inhibitors in malignant prostate cell lines, primary cultured prostatic cells and prostatic tissue. *Eur J Cancer* 35: 138–144.
10. Garcia-Calvo M, Peterson E P, Leiting B, Ruel R, Nicholson D W, Thornberry N A (1998). Inhibition of human caspases by peptide-based and macromolecular inhibitors. *J Biol Chem* 273: 32608–32613.
11. Green D R, Reed J C (1998). Mitochondria and apoptosis. *Science* 281: 1309–1312.
12. Guitiérrez M I, Cherney B, Hussain A, Mostowski H, Tosato G, Magrath I, Bhatia K (1999). Bax is frequently compromised in Burkitt's lymphomas with irreversible resistance to Fas-induced apoptosis. *Cancer Res* 59: 696–703.
13. Heidtmann H H, Salge U, Abrahamson M, Bencina M, Kastalic L, Kopitar-Jerala N, Turk V, and Lah T T (1997). Cathepsin B and cysteine protease inhibitors in human lung cancer cell lines. *Clin Exp Metastasis* 15: 368–381.
14. Henkart P A (1996). ICE family protease: mediators of all apoptotic death? *Immunity* 4: 195–201.
15. Isahara K, Ohsawa Y, Kanamori S, Shibata M, Waguri S, Sato N, Gotow T, Watanabe T, Momoi T, Urase K, Kominami E, and Uchiyama Y (1999). Regulation of a novel pathway for cell death by lysosomal aspartic and cysteine proteases. *Neuroscience* 91: 233–249.
16. Jones B, Roberts P J, Faubion W A, Kominami E, and Gores G J (1998). Cystatin A expression reduces bile salt-induced apoptosis in a rat hepatoma cell line. *Am J Physiol* 275: G723–730.
17. Keppler D, Sameni M, Moin K, Mikkelsen T, Diglio C, and Sloane B (1996). Tumor progression and angiogenesis: cathepsin B & Co. *Biochem Cell Biol* 74: 799–810.
18. Kos J. and Lah T T (1998). Cysteine proteinase and their endogenous inhibitors: Target proteins for prognosis, diagnosis and therapy in cancer (Review). *Oncol Rep* 5: 1349–1361.
19. Li P, Nijhawan D, Budihardjo I, Srinivasula S M, Ahmad M, Alnemri E, Wang X (1997). Cytochrome c and dATP-dependent formation of Apaf-1/caspase-9 complex initiates an apoptotic protease cascade. *Cell* 91: 479–489.
20. Lowe S W, Ruley H E, Jacks T, Housman D E (1993a). p53-dependent apoptosis modulates the cytotoxicity of anticancer agents. Cell 74: 957–967.
21. Lowe S W, Schmitt E M, Smith S W, Osborne B A, Jacks T (1993b). p53 is required for radiation-induced apoptosis in mouse thymocytes. Nature 362: 847–849.
22. Magi-Galluzzi C, Montironi R, Cangi M G, Wishnow K, Loda M (i998). Mitogen-activated protein kinases and apoptosis in PIN. *Virchows Arch* 432: 407–413.
23. Makarewicz R, Drewa G, Szymanski W, and Skonieczna-Makarewicz 1 (1995). Cathepsin B in predicting the extent of the cervix carcinoma. *Neoplasma* 42: 21–24.
24. Meijerink J P, Mensink E J, Wang K, Sedlak T W, Sloetjes A W, de Witte T, Waksman G, Korsmeyer S J (1998). Hematopoietic malignancies demonstrate loss-of-function mutations of BAX. *Blood* 91: 2991–2997.
25. Memon S A, Moreno M B, Petrak D, Zacharchuk C M (1995). Bcl-2 blocks glucocorticoid—but not as Fas—or activation-induced apoptosis in a T cell hybridoma. *J Immunol* 155: 4644–4652.
26. Mort J S, and Buttle D J. Cathepsin B (1997). *Int J Biochem Cell Biol* 29: 715–720.
27. Peller S (1998). Clinical implications of p53: effect on prognosis, tumor progression and chemotherapy response. Cancer Biol. 8: 379–387.
28. Pronk G J, Ramer K, Amiri P, Williams L T (1996). Requirement of an ICE-like protease for induction of apoptosis and ceramide generation by REAPER. *Science* 271: 808–810.
29. Roberts L R, Kurosawa H, Bronk S F, Fesmier P J, Agellon L B, Leung W-Y, Mao F, and Gores G J (1997). *Gastroenterology* 113: 1714–1726.
30. Rooprai H K, and McCormick D (1997). Proteases and their inhibitors in human brain tumors: a review. *Anticancer Res* 17: 4151–4162.
31. Sameni M, Elliott E, Ziegler G, Fortgens P H, Dennison C and Sloane B F (1995). Cathepsin B and cathepsin D are localized at the surface of human breast cancer cells. *Pathol Oncol Res* 1: 43–53.
32. Schlegel J, Peters I, Orrenius S, Miller D K, Thormberry N A, Yamin T T, Nicholson D W (1996). CPP32/apopain is a key interleukin 1 beta converting enzyme-like protease involved in Fas-mediated apoptosis. *J Biol Chem* 271: 1841–1844.
33. Shibata M, Kanamori S, Isahara K, Ohsawa Y, Konishi A, Kametaka S, Watanabe T, Ebisu S, Ishido K, Kominami E, and Uchiyama Y (1998). Participation of cathepsins B and D in apoptosis of PC12 cells following serum deprivation. *Biochem Biophys Res Commun* 251: 199–203.
34. Slee E A, Zhu H, Chow S C, MacFarlane M, Nicholson D W, Cohen G M (1996). Benzyloxycarbonyl-Val-Ala-Asp (OMe) fluoromethylketone (Z-VAD.FMK) inhibits apoptosis by blocking the processing of CPP32. *Biochem J* 315: 21–24.
35. Sloane B F, Moin F, Sameni M, Tait L R, Rozhin J, and Ziegler G (1994). Membrane-association of cathepsin B can be induced by transfection of human breast cells with c-Ha-ras oncogene. *J Cell Sci* 107: 373–384.
36. Strohmaier A R, Porwol T, Acker H, and Spiess E (1997). Tomography of cells by confocal laser scanning microscopy and computer-assisted three-dimensional image resonstruction: localization of cathepsin B in tumor cells penetrating collagen gels in vitro. *J Histochem Cytochem* 45: 975–983.
37. Thornberry N A, Lazebnik Y (1998). Caspases: enemies within. *Science* 281: 1312–1316.
38. Uckun F M, Waddick K G, Mahajan S, Xiao J, Takata M, Bolen J, Kurosaki T (1996). BTK is a mediator of radiation-induced apoptosis in DT-40 lymphoma B cells. *Science* 273: 1096–1100.
39. Vasilakos J P, Ghayur T, Carroll R T, Giegel D A, Saunders J M, Quintal L, Keane K M, Shivers B D (1995). IL-1 beta converting enzyme (ICE) is not required for apoptosis induced by lymphokine deprivation in an IL-2 dependent T cell line. *J Immunol* 155(7): 3433–3442.
40. Weiss R E, Liu B C, Ahlering T, and Dubeau M J (1990). Mechanism of human bladder tumor invasion: role of protease cathepsin B. *J Urol* 144: 798–804.

41. Xia Z, Dickens M, Raingeaud J, Davis R J, Greenberg M E (1995). Opposing effects of ERK and JNK-p38 MAP kinases on apoptosis. *Science* 270: 1326–1331.
42. Yan S, Sameni M. and Sloane B F (1998). Cathepsin B and human tumor progression. *Biol Chem* 379: 113–123.
43. Zhu D-M, Fang W-H, Narla R-K, and Uckun F M (1999). A requirement for protein kinase C inhibition for calcium-triggered apoptosis in Acute lymphoblastic leukemia cells. *Clin Can Res* 5: 355–360.
44. Zuo H, Henzel W J, Liu X, Lutschg A, Wang X (1997). Apaf-1, a human protein homologous to *C. elegans* CED-4, participates in cytochrome c-dependent activation of caspase-3. *Cell* 90: 405–413.

We claim:

1. A method of inducing apoptosis in a cancer cell comprising contacting the cell with an apoptosis inducing amount of a cathepsin inhibitor, wherein the cathepsin inhibitor is CATI-1 (Z-Phe-Gly-NHO-Bz; where Z is benzyloxycarbonyl, —NHO— is hydroxylamine linkage, and Bz is benzoyl).

2. The method of claim 1, wherein the cancer is a solid tumor.

3. The method of claim 2, wherein the cancer is prostate cancer.

4. The method of claim 2, wherein the cancer is breast cancer.

5. The method of claim 2, wherein the cancer is a brain tumor.

6. The method of claim 1, wherein the cancer is a leukemia.

7. A method of treating cancer cells in a subject comprising administering a therapeutically effective amount of a cathepsin inhibitor, wherein said treating induces apoptosis of cancer cells, and wherein the cathepsin inhibitor is CATI-1 (Z-Phe-Gly-NHO-Bz; where Z is benzyloxycarbonyl, —NHO— is hydroxylamine linkage, and Bz is benzoyl).

8. The method of claim 7, wherein the cancer is a solid tumor.

* * * * *

UNITED STATES PATENT AND TRADEMARK OFFICE
CERTIFICATE OF CORRECTION

PATENT NO. : 6,605,589 B1
DATED : August 12, 2003
INVENTOR(S) : Uckun et al.

It is certified that error appears in the above-identified patent and that said Letters Patent is hereby corrected as shown below:

Title page,
Item [56], References Cited, OTHER PUBLICATIONS, "Blandino", reference "Mutuant" should read -- Mutant -- and "*Onogene*" should read -- *Oncogene* --; "Mizuochi", reference "fo rdegradation" should read -- for degradation --; and "Andreason", reference "Asa" should read -- As a --

Column 1,
Line 41, "Isahara et at." should read -- Isahara et al. --

Signed and Sealed this

Twenty-seventh Day of January, 2004

JON W. DUDAS
*Acting Director of the United States Patent and Trademark Office*